US006640211B1

(12) United States Patent
Holden (10) Patent No.: US 6,640,211 B1
(45) Date of Patent: Oct. 28, 2003

(54) GENETIC PROFILING AND BANKING SYSTEM AND METHOD

(75) Inventor: Arthur L. Holden, Winnetka, IL (US)

(73) Assignee: First Genetic Trust Inc., Deerfield, IL (US)

(*) Notice: Subject to any disclaimer, the term of this patent is extended or adjusted under 35 U.S.C. 154(b) by 0 days.

(21) Appl. No.: 09/425,085

(22) Filed: Oct. 22, 1999

(51) Int. Cl.$^7$ .............................................. G06F 17/60
(52) U.S. Cl. ........................................................ 705/1
(58) Field of Search .............................. 435/5, 6; 705/3

(56) References Cited

U.S. PATENT DOCUMENTS

| | | | | |
|---|---|---|---|---|
| 4,683,195 A | * | 7/1987 | Mullis et al. .................. 435/6 |
| 5,050,613 A | * | 9/1991 | Newman et al. ............. 600/483 |
| 5,523,208 A | * | 6/1996 | Kohler et al. .................. 435/6 |
| 5,834,181 A | * | 11/1998 | Shuber .......................... 435/5 |
| 5,876,926 A | * | 3/1999 | Beecham .................... 382/115 |
| 5,897,989 A | * | 4/1999 | Beecham .................... 382/115 |
| 5,920,871 A | * | 7/1999 | Macri et al. ............. 707/104.1 |
| 5,924,074 A | | 7/1999 | Evans ............................ 705/3 |
| 5,941,947 A | * | 8/1999 | Brown et al. ................ 709/225 |
| 5,993,387 A | * | 11/1999 | Moore et al. .................... 435/2 |
| 6,073,106 A | * | 6/2000 | Rozen et al. .................... 705/2 |
| 6,253,203 B1 | * | 6/2001 | O'Flaherty et al. ........... 707/10 |

FOREIGN PATENT DOCUMENTS

| | | | |
|---|---|---|---|
| EP | 0913758 | 5/1999 | |
| JP | 10239300 A | * 9/1998 | .......... G01N/30/88 |
| WO | 97/31327 | 8/1997 | |
| WO | WO 9850154 A1 | * 11/1998 | ............. B01L/3/00 |

OTHER PUBLICATIONS

Pulst, S.M., 1999 Neurol., vol. 56, No. 6, "Genetic Linkage Analysis", pp. 667–672.*

Pulst, S.M., 1999 Neurol., vol. 56, No. 6, "Genetic Linkage Analysis", pp. 667–672.

Ballantyne, et al., 1997 J. Cardiovasc. Risk, vol. 4, No.5–6, "Molecular Markers for Atherosclerosis", pp. 353–356.

Marian, A.J. 1997 J. Cardiovasc. Risk, vol. 4, No. 5–6, "Genetic Markers: Genes Involved in Human Hypertension", pp. 341–345.

Marian, A.J. 1997 J. Cardiovasc. Risk, vol. 4, No. 5–6, "Genetic Markers: Genes Involved in Atherosclerosis", pp. 333–339.

Hallman, D.M.,et al., 1997 J. Cardiovasc. Risk, vol. 4, No. 5–6, "Molecular and Genetic Approaches to the Study of Cardiovascular Disease", pp. 325–331.

Ballantyne, et al., 1997 J. Cardiovasc. Risk, vol. 4, No.5–6, "Genetic and Molecular Markers for Vascular Disease", pp. 321–323.

Zehbe, et al., 1999 Lancet, vol. 354 (9174), "Condon 72 Polymorphism of p53 and Its Association with Cervical Cancer", pp. 218–219.

Hakansson, et al., 1997 Am. J. Hum. Genet., vol. 60, No. 5, "Moderate Frequency of BRCA1 and BRCA2 Germ–Line Mutations in Scandinavian Familial Breast Cancer", pp. 1068–1078.

Vaidya, et al. 1999 Lancet, vol. 354 (9180), "Cytotoxic T Lymphocyte Antigen–4 (CTLA–4) Gene Polymorphism Confers Susceptibility to Thyroid Associated Orbitopathy", pp. 743–744.

(List continued on next page.)

Primary Examiner—John G. Weiss
Assistant Examiner—Jonathan Ouellette
(74) Attorney, Agent, or Firm—Ropes & Gray LLP; Edward J. Kelly; Agnes S. Lee (57) ABSTRACT

A genetic banking system allows the ability to securely store genetic profile data while allowing access to individuals authorized to access the profile for authorized purposes.

20 Claims, 4 Drawing Sheets

OTHER PUBLICATIONS

Liao, et al., 1999 Angiology, vol. 50, No. 8, "A Missense Mutation of the Nitric Oxide Synthase (eNOS) Gene (Glu298Asp) in Five Patients with Coronary Artery Disease", pp. 671–676.

Rust, et al., 1999 Nat. Genet, vol. 22, No. 4, "Tangier Disease id Caused by Mutations in the Gene Encoding ATP–Binding Cassette Transporter 1", pp. 352–355.

Brooks–Wilson, 1999 Nat. Genet., vol. 22, No. 4, "Mutations in ABC1 Tangier Disease and Familial High–Density Lipoprotein Deficiency", pp. 336–345.

Ligers, et al., 1999 Neuroimmunol., vol. 97(1–2), "The CTLA–4 Gene is Associated with Multiple Sclerosis", pp. 182–190.

Shinar, et al., 1998 J. Mol. Neurosci., vol. 11, No. 3, "Analysis of Allelic Association Between D6S461 Marker and Multiple Sclerosis in Ashkenazi and Iraqi Jewish Patients", pp. 265–269.

Schutte, et al, 1999 Am. J. Med. Genet., vol. 84, No. 2, "Microdeletions at Chromosome Bands 1q32–q41 As A Cause of Van der Woude Syndrome", pp. 145–150.

Aita, et al., 1999 Am. J. Hum. Genet., vol. 64, No. 1, A Comprehensive Linkage Analysis of Chromosome 21q22 Supports Prior Evidence for A Putative Bipolar Affective Disorder Locus, pp. 210–217.

Campbell, et al., 1999 Mol. Psychiatry, vol. 4, No. 1, "Association Between A Marker in the UCP–2/UCP–3 Gene Cluster and Genetic Susceptibility to Anorexia Nervosa", pp. 68–70.

Scacchi, et al., 1999 Neurosci. Lett., vol. 259, No. 1, "Plasma Levels of Apolipoprotein E and Genetic Markers In Elderly Patients With Alzheimer's Disease", pp. 33–36.

Kruger, et al., 1999 Ann. Neurol., vol. 45, No. 5, "Increased Susceptibility to Sporadic Parkinson's Disease By A Certain Combined α–Synuclein/Apolipoprotein E Genotype", pp. 611–617.

* cited by examiner

GENETIC PROFILING AND BANKING SYSTEM AND METHOD

BACKGROUND OF THE INVENTION

This invention relates to a system for profiling and banking genetic information about individuals.

Genetic information derived from a sample can be used to determine medical and other information about an individual. Obtaining genetic samples and testing those samples raises concerns about privacy, access, and the use of the resulting information. Such information could, however, be useful for individuals and medical practitioners.

Currently there are companies that provide banking services for storing physical samples of genetic material from biological tissue, such as blood or cheek cells. That material can be retrieved from storage and tested as desired. Removing the sample and having it tested is time consuming and may be repetitive if multiple tests are needed over time.

SUMMARY OF THE INVENTION

The present invention includes systems and methods for storing and accessing genetic information. The systems and methods preferably provide protection against unauthorized access and use, but provide convenience in accessing and using genetic information if such use is properly authorized.

In a method according to the present invention, a patient enrolls in a genetic banking system and provides a source of genetic material, such as a blood sample. The sample is processed using a combination of experimental and/or in silico techniques to produce a genetic profile for the patients. The processed data is stored in a database to create a genetic profile for that patient. A remaining portion of the physical sample may also be stored for further use if needed.

The patient, either at the time of enrollment or after a sample is processed, can dictate access rights, including the ability of third parties (other than the individual or the genetic bank itself), such as medical practitioners, to access this profile, and the specific purposes for which the profile can be accessed and used. Thus, the patient can specify both the people who will have access, and the uses for which they have access.

The system provides user interfaces for the user to enter identification information and access rights. The bank can prepare standard protocols that describe allowed and proscribed data sharing.

A medical practitioner authorized to have access by the patient and confirmed by the access control system can access the profile that is stored and can run tests based on the profile as stored in the database; for example, such a test can be run to determine the presence or absence of certain markers.

In another aspect, a system according to the present invention includes a database for storing genetic data on individuals and an access control system that controls access to the database and manages the tests that are to be done. The control system interacts with (or includes) a testing system to cause the testing system to process the profile data to conduct the desired test. The control system authorizes the test and provides the results.

The system allows users to store a comprehensive digitized DNA profile based on a sample, in addition to storage of physical samples. The patient has control to voluntarily allow access to particular people and for particular purposes, thus protecting the privacy of that information. Because the samples have been processed and digitized, additional tests can be performed without requiring repetitive use of actual physical samples. Other features and advantages will become apparent from the following description of preferred embodiments, drawings, and claims.

DESCRIPTION OF PREFERRED EMBODIMENTS

Figure 1:
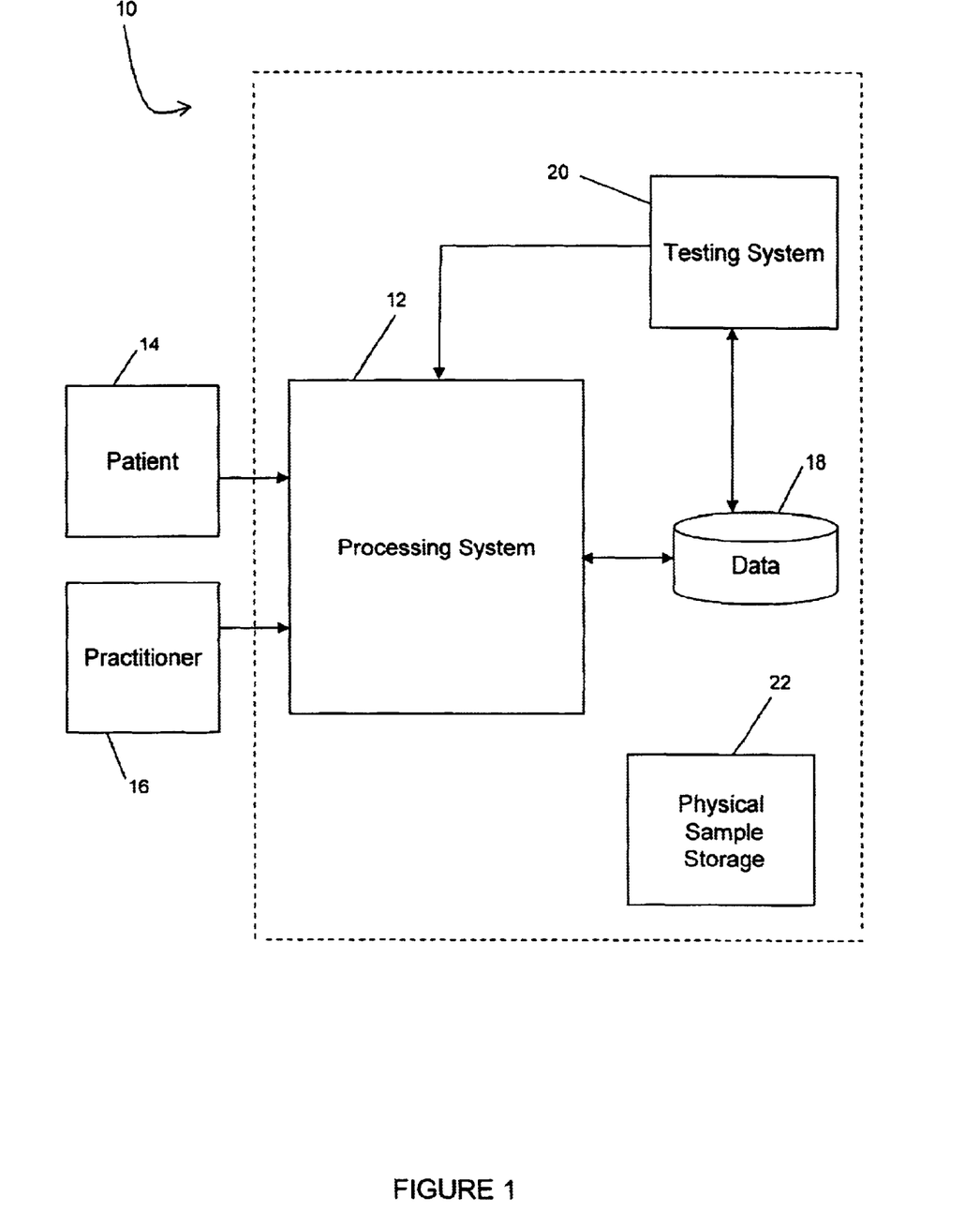
FIG. 1 is a block diagram of a system according to the present invention.

A genetic banking system 10 has a database 18 for storing genetic profiles, and a processing system 12 for controlling interactions between a patient 14 and database 18, and between a medical practitioner 16 and database 18. System 10 may also include data integration and analysis functionalities and a testing system 20 that is linked to database 18, and may also include physical storage 22 for storing physical samples of genetic material. Processing system 12 maintains access rights that allow a patient to specify and control the access to the profile by others such as medical practitioners, enforces the access rights that are voluntarily provided from the patient, causes testing system 20 to perform a desired test, and provides results to the medical practitioner.

Database 18 may be a relational database with a relational database management system (RDBMS), or it may use technology such as that in ACEDB, a genome database system that has a custom database kernel, a data model designed specifically for handling scientific data flexibly, and a graphical user interface with many specific displays and tools for genomic data. ACEDB software and supporting tools are publicly available via the Internet by download.

Processing system 12 and the testing system 20 may each include a special purpose computer, a workstation, a server, or some combination of linked computers, workstations, and/or servers for interfacing with users, processing, information and performing tests. The connections employed are preferably high speed, TCP/IP connections, such as T1 lines. The testing system may be independent and remote from processing system 12 that interacts with users and medical practitioners, or the testing system and processing system may be part of one larger processing system.

Figure 2:
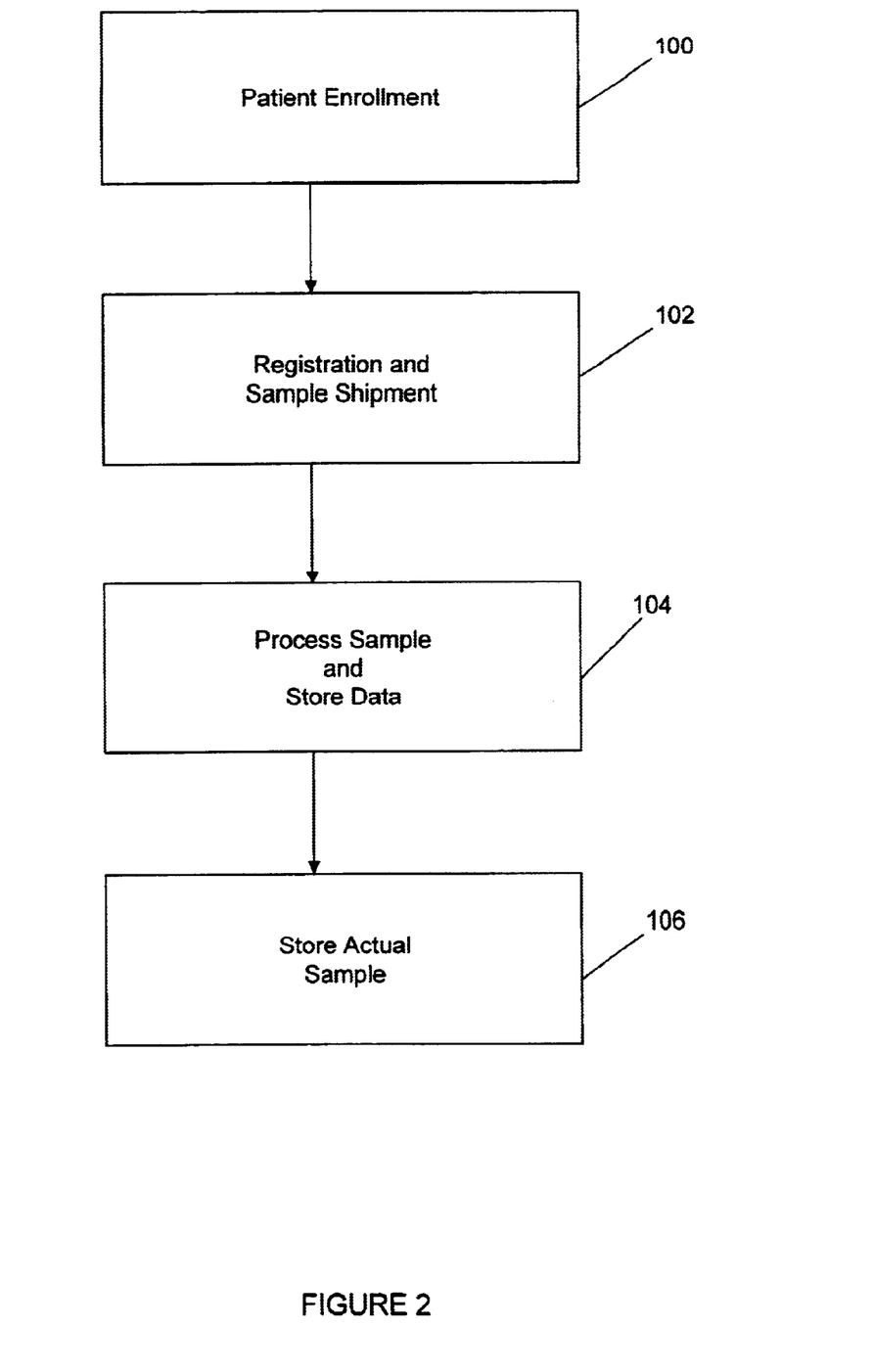
FIGS. 2–4 are flow charts showing methods according to the present invention.

Referring to the flow chart of FIG. 2, a source of genetic material, such as a blood sample, is provided by a patient for testing purposes after the patient enrolls with the system (100). This enrollment process includes the processing system providing a user interface to the patient, and the patient providing information about himself/herself through the user interface to the processing system about himself/herself. The patient, using the user interface, voluntarily establishes conditions under which the genetic information can be accessed, preferably through use of a menu of standard proptocols or by selecting a standard protocol and customizing it. The patient can thus determine access rights, including both who gets access and the uses that can be made of that genetic information. Thus, at least some authorized third parties users may have access for some purposes and not for other purposes, or some third parties may have access rights set to "all" for all purposes.

To confirm selections regarding access and use made by the patients, the system preferably employs a process of querying and confirming through the user interface, and preferably also includes information for the patient about the system and about the tests. Redundancies and checks can be provided in the interaction between the patient and the user interface during the enrollment process so that the patient understands the possible uses of the profile and the consequences of selecting who gets access and the uses for that access.

To enroll, the patient preferably either obtains from the processing system a password at the time of enrollment, or the patient may have previously been provided with a password for confidentiality. The system preferably provides a high level of security and may include mechanisms such as digital certificates in addition to the password protection. The enrollment can take place on a private or other closed or dedicated network, such as a LAN or Intranet, or with appropriate security measures, over the Internet, and can be performed without additional human intervention (i.e., additional to the user). For Internet interaction, the processing system can include a web server for providing pages or forms and for receiving information entered onto those forms.

When the patient is enrolled, the patient has a physical source of genetic material shipped to the genetic banking system or some other desired location for processing (102).

At a later time, the patient can use the password or a new password to change selections for who can get access and the uses for which access can be made. In addition, the selections can "time out" such that the user must re-confirm selections after some period of time or else the access rights are terminated.

The physical sample is processed by the testing system and the results of the processing are stored in the database (104). The processing that is performed on the sample can vary depending on the genetic banking and testing services that are provided, but can include genotyping and bioinformatic profiling of general and/or specific genetic marker panels. Such information can be used to determine risks of many diseases including, without limitation, cancer, Huntington's Disease, Alzheimer's Disease, and hypertension. The tests can be done through a number of different methods, such as fluorescence, optical density, mass spectroscopy, DNA sequencing, microarray-based assays, or other current methods or methods to be developed. The data that is provided from these tests is digitally stored in the database as a genetic profile of the patient for subsequent analysis and tests.

After the tests are done, the actual physical sample (or at least any remaining portion) may be stored if desired in case it is needed for confirmation or other future purposes (106). This physical storage can be done using known cryogenic techniques.

Figure 3:
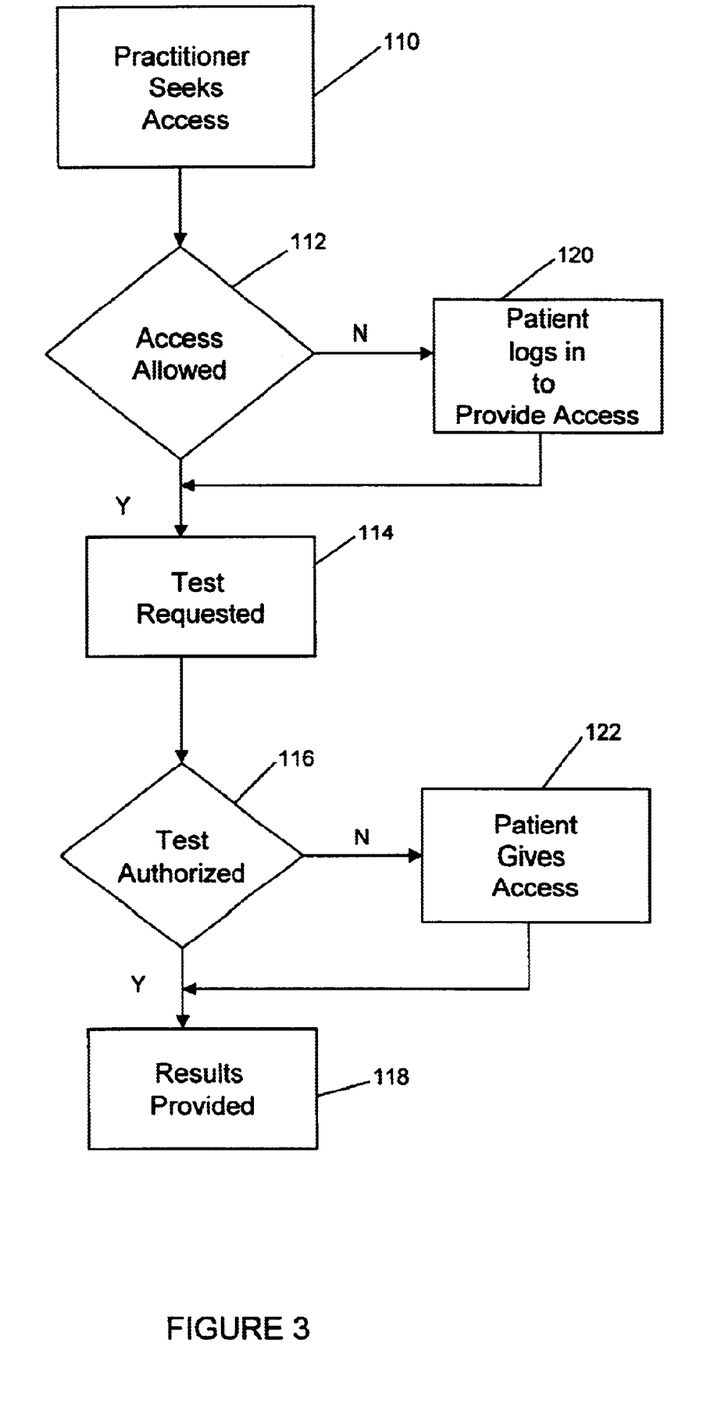

Referring to FIG. 3, a third party, such as a medical practitioner (i.e., a party other than the patient or people associated with the management and/or operation of the genetic banking system), may seek access to an enrolled individual's profile in the database (110) using a user interface provided from the processing system to the practitioner. The practitioner is authenticated, such as through the use of digital certificates and/or password protection before he/she can access the information. The system compares the access rights entered by the patient into the system with that third party practitioner seeking access to the patient's profile. The system then determines whether access is allowed for that third party practitioner (112).

If the access is allowed, the practitioner can seek to have a test performed, such as a search of the profile for markers for Huntington's Disease (114). The system determines whether the test is authorized by comparing the type of test that is desired with the access rights entered by the patient (116) (a practitioner may have access for some purposes but not others). If the test is authorized, the processing system forwards the request to the testing system to perform the test. The results of the test can be analyzed in the processing system if needed and provided to the practitioner, preferably in an encrypted form (118). The connections that are provided, particularly between database 18 and testing system 20, should have high bandwidth to allow a significant amount of data to be quickly provided to the testing system for the results. Testing system 20 should be sufficiently computationally intensive in order to perform the requested tests.

If access by the practitioner is not allowed, or if the particular test is not authorized, the patient can log in to the system to provide the appropriate authorizations for access (120, 122).

The practitioner can seek access over a dedicated or closed network, or with appropriate security, over the Internet. The processes of seeking access, confirming access, performing the test, and reporting results can all be performed without additional human intervention (other than the medical practitioner himself/herself).

The patient may or may not have access to have tests run individually and without the tests being performed for a medical practitioner. It may be desirable for the patient only to have access through a medical practitioner who can explain to the patient the actual meaning of the tests. However, it would also be possible to allow the patient to have tests performed and to have access to the results.

Figure 4:
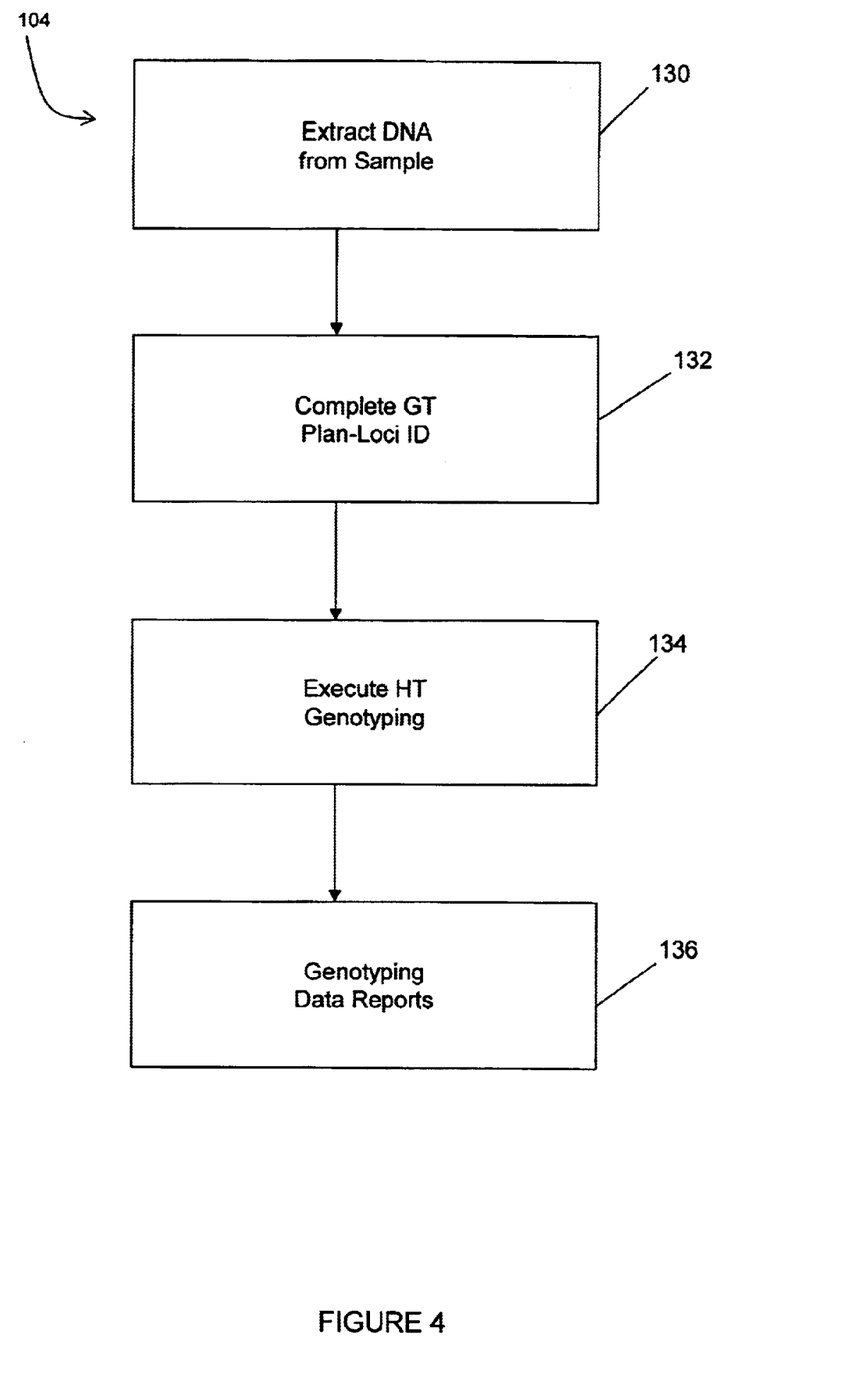

Referring to FIG. 4, a more detailed example of the sample processing process (104) is shown. In this process, the DNA is extracted from the sample, such as the blood sample (130). Extraction of DNA from a sample of cells may be accomplished by any standard method. Using the patient's DNA sample, a complete genotype (GT) and pan-loci ID are performed (132). For example, a single nucleotide polymorphism (SNP) map may be generated from the patient's DNA sample. In the alternate, if the patient has or is predisposed to develop a specific disease, genes (e.g., mutations, aberrant expression patterns) associated with those diseases may be directly sequenced from the patient's sample. Next, high-throughput (HT) genotyping is executed (134). The results of the genotyping data are provided in reports that are preferably customized for convenient use (136).

Several non-limiting genes, and the diseases with which they are associated, which can be sequenced and/or from which a SNP map can be generated according to the methods of the invention are provided in Pulst S. M. (1999) Neurol. 56(6): 667–672; Ballantyne et al. (1997) J. Cardiovasc. Risk 4(5–6):353–356; Marian, A. J. (1997) J. Cardiovasc. Risk 4(5–6): 341–345; Marian, A. J. (1997) J. Cardiovasc. Risk 4(5–6): 333–339; Hallman, D. M. et al. (1997) J. Cardiovasc. Risk 4(5–6): 325–331; Ballantyne et al. (1997) J. Cardiovasc. Risk 4(5–6): 321–323. Additional genes the diseases with which they are associated are listed in Table I.

TABLE 1

| Gene | Disease | Reference* |
|---|---|---|
| p53 | cervical cancer | Zehbe et al. (1999) Lancet 354(9174): 218–219 |

TABLE 1-continued

| Gene | Disease | Reference* |
|---|---|---|
| BRCA1 | breast cancer | Hakansson et al. (1997) Am. J. Hum. Genet. 60(5): 1068–1078 |
| BRCA2 | breast cancer | Hakansson et al. (1997) Am. J. Hum. Genet. 60(5): 1068–1078 |
| CTLA-4 | thyroid associated orbitopathy | Vaidya et al. (1999) Lancet 354(9180): 743–744 |
| nitric oxide synthase (eNOS) | coronary artery disease | Liao et al. (1999) Angiology 50(8): 671–676 |
| gene encoding human ATP cassette-binding transporter 1 (ABC) | Tangier disease | Rust et al. (1999) Nat. Genet. 22(4): 352–355; Brooks-Wilson (1999) Nat. Genet. 22(4):336–345 |
| CTLA-4 | multiple sclerosis | Ligers et al. (1999) J. Neuroimmunol. 97(1–2): 182–190 |
| genetic marker D6S461 | multiple sclerosis | Shinar et al. (1998) J. Mol. Neurosci. 11(3): 265–269 |
| Microdeletions at chromosome bands 1q32–q41 | Van der Woude syndrome | Schutte et al. (1999) Am. J. Med. Genet. 84(2):145–150 |
| chromosome 21q22 | bipolar affective disorder | Aita et al. (1999) Am. J. Hum. Genet. 64(1):210–217. |

*each reference is hereby incorporated by reference

In addition to specific genes associated with specific diseases, many diseases are characterized by their association with a set of at least one genetic marker which can be detected using the methods of the present invention. For example, a marker in the UCP-2/UCP-3 gene cluster has been linked to a genetic susceptibility to anorexia nervosa (Campbell et al. (1999) Mol. Psychiatry 4(1): 68–70). Likewise, genetic markers in addition to apolipoprotein E (APOE) polymorphism has been associated with Alzheimer's disease (Scacchi et al. (1999) Neurosci. Lett. 259(1): 33–36). Parkinson's disease is similarly associated with a certain combined alpha-synuclein/apolipoprotein E genotype (Kruger et al. (1999) Ann. Neurol. 45(5): 611–617). The methods of the invention may also be employed to detect the presence of a multigeneic disease (or the predisposition to develop such a disease) that is associated with and/or caused by the allelic variants of more than one gene.

For the purposes of the invention, it matters not whether the disease is caused by and/or correlated with the associated genetic marker or whether the associated genetic marker is caused by and/or correlated with the disease. What is relevant is that certain genetic markers, such as allelic variants, are associated with certain disease phenotypes and/or predisposition to develop the disease.

The invention provides an accessible confidential database that creates and stores genetic information, such as an SNP map, from patient DNA. As more patient samples are added to the database of the invention, and as researchers find more associations between genetic markers and particular disease phenotypes, use of the invention provides an on-going self-perpetuating advancement into the development of associations between genetic markers and certain diseases. Moreover, with appropriate security and privacy cautions, the database can be used in an anonymous manner to allow researchers to access a body of genetic information for research and analysis purposes.

The system of the present invention thus allows a patient to voluntarily bank genetic information that can be used quickly to determine genetic and medical information about that individual, particularly information that relates to whether the individual carries genetic information associated with known diseases. The system provides restrictions, however, that allow the user to retain privacy and limit unauthorized access to his/her genetic information. The system is thus unlike a system, for example, in which DNA information, like fingerprint information, is stored for identification purposes to use DNA information to identify individuals involved in specific criminal activities; in such a case, the individual who provides the sample would generally not have voluntary control to establish the ability of others to access the information, and such systems would generally not have the ability to test for a number of different medical purposes for which the DNA information can be accessed by others.

The patents and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Having described a preferred embodiment of the present invention, it should be apparent that modifications can be made without departing from the scope of the invention as defined by the appended claims. For example, the authorization is described as a two-step process of checking the user then the purpose, although the authorization could combine user and purpose into one combined access right. While components of the preferred embodiment may have certain benefits and advantages noted herein, other systems and components thereof may nonetheless be within the scope of the claims without necessarily having each and every one of the noted benefits and advantages.

What is claimed is:

1. A method comprising
   processing a user's physical sample with genetic information to produce a genetic profile of data representative of the genetic information in the physical sample;
   storing the genetic profile in an accessible database;
   receiving from the user a set of access rights defining conditions under which third party users can access the genetic profile, said conditions including conditions representative of the users allowed access and uses for which access is allowed;
   receiving a request from a third party user to perform a test on the genetic profile;
   comparing the third party user's request with the access rights to confirm that the third party user is authorized to access the genetic profile as requested;
   if the third party user is authorized, performing the requested test on the genetic profile and reporting the results to the third party user; and
   if the third party user is not authorized, denying access.

2. The method of claim 1, wherein performing a requested test includes identifying in the genetic profile one of a number of genetic markers in the genetic profile associated with certain disease phenotypes.

3. The method of claim 1, wherein receiving a request includes receiving a request over the Internet, wherein the receiving, comparing, performing, and reporting are performed without additional human intervention.

4. The method of claim 1, further comprising providing to the user a user interface to allow the user to enroll with the system to establish the access rights.

5. The method of claim 4, wherein the enrollment is performed over the Internet without additional human intervention.

6. The method of claim 1, wherein the processing includes performing one or more of fluorescence, optical density, mass spectroscopy and DNA sequencing.

7. The method of claim 1, wherein performing a requested test includes identifying in the genetic profile one or more of the genes identified in Table 1.

8. A method comprising:
receiving over the Internet from a third party user a request to perform a medical test on a stored genetic profile or a patient to determine the presence or absence of a gene or marker associated with a specified disease;
determining whether the third party user is authorized to access the genetic profile for the purpose of the requested medical test based on stored access rights provided by the patient and including information representative of the users allowed access to the genetic profile and uses for which access is allowed; if the third party user is authorized for access and to perform the test, performing the test on the genetic profile and reporting the results to the third party user requesting the test information; and if the third party user is not authorized for access and to perform the test, denying access to the third party user and not performing the test.

9. The method of claim 8, further comprising providing to the user a user interface to allow the user to voluntarily enter information to establish access rights.

10. The method of claim 9, wherein the entry of information is performed without additional human interventions.

11. The method of claim 8, wherein the access rights include at least one third party that has rights to access the genetic profile for purposes of performing some medical tests and not for performing other medical tests.

12. The method of claim 8, wherein performing the test includes determining whether a specific genetic marker is present.

13. The method of claim 8, wherein performing the test includes determining whether a specific gene is present.

14. A system comprising:
a database for storing genetic profiles of patients;
a testing system for performing medical tests on genetic profiles; and
a processing system;
providing to the patient a user interface for the patient to voluntarily enter information to establish access rights including conditions representative of the users allowed access and uses for which access is allowed, for authorizing access by third party users for purposes which the third party users can gain access,
using the access rights to control access to the database when access is requested by third party users,
in response to a request by a third party user for a test on the genetic profile, checking the access rights to determine whether the third party is authorized and whether the test is authorized, and,
if the third party is authorized and providing test results to the authorized entity.

15. The system of claim 14, wherein the profiles are stored in such a way that one or more of a plurality of genetic markers associated with specific diseases can be identified.

16. The system of claim 14, wherein the processing system includes a web server for providing the user interface to the patient.

17. The system of claim 14, wherein the processing system provides a third party interface to the third party for seeking access without additional human intervention.

18. The system of claim 14, wherein the genetic profiles include SNP maps.

19. The system of claim 14, wherein the user can establish access rights and the third party can try to obtain access all without additional human intervention.

20. A method comprising:
processing a user's physical sample with genetic information to produce a genetic profile of data representative of the genetic information in the physical sample;
storing the genetic profile in an accessible database;
receiving from the user a set of access rights defining conditions under which users can access the genetic profile, said access rights including conditions representative of the users allowed access and uses for which access is allowed;
receiving a request to perform a test on the genetic profile;
comparing the request with the access rights to confirm that user is authorized to access the genetic profile as requested;
if the user is authorized, performing the requested test on the genetic profile and reporting the results to the user; and
if the user is not authorized, denying access.

* * * * *

UNITED STATES PATENT AND TRADEMARK OFFICE
CERTIFICATE OF CORRECTION

PATENT NO. : 6,640,211 B1 Page 1 of 1
DATED : October 28, 2003
INVENTOR(S) : Arthur L. Holden It is certified that error appears in the above-identified patent and that said Letters Patent is hereby corrected as shown below:

Column 6,
Line 52, change "performing" to -- causing the testing system to automatically perform --.

Column 7,
Line 13, change "or a patient" to -- of a patient --.
Line 22, change "performing" to -- causing the testing system to automatically perform --.
Line 45, change "testing system" to -- testing means system --.

Column 8,
Line 11, after "authorized" insert -- causing the testing means system to automatically perform the test --.
Line 41, change "performing" to -- causing the testing system to automatically perform --.

Signed and Sealed this

Sixteenth Day of August, 2005

JON W. DUDAS
*Director of the United States Patent and Trademark Office*